United States Patent
Niklaus et al.

(10) Patent No.: US 11,027,059 B2
(45) Date of Patent: Jun. 8, 2021

(54) SPRING FORCE ASSEMBLY FOR BIASING OR ACTUATING STOPPERS OF SYRINGES, INJECTION PEN CARTRIDGES AND THE LIKE

(71) Applicant: Roche Diagnostics International AG, Rotkreuz (CH)

(72) Inventors: Hanspeter Niklaus, Riken (CH); Florian Schaad, Oberbipp (CH); David Teutsch, Schuepfen (CH)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 255 days.

(21) Appl. No.: 14/466,256

(22) Filed: Aug. 22, 2014

(65) Prior Publication Data
US 2014/0364808 A1    Dec. 11, 2014

Related U.S. Application Data

(63) Continuation of application No. PCT/EP2012/053293, filed on Feb. 27, 2012.

(51) Int. Cl.
*A61M 5/145* (2006.01)
*A61M 5/20* (2006.01)
*A61M 5/24* (2006.01)
*A61M 5/315* (2006.01)

(52) U.S. Cl.
CPC ........ *A61M 5/1454* (2013.01); *A61M 5/2033* (2013.01); *A61M 5/24* (2013.01); *A61M 5/3159* (2013.01); *A61M 5/31565* (2013.01); *A61M 5/31576* (2013.01); *A61M 2005/14506* (2013.01)

(58) Field of Classification Search
CPC ............ A61M 5/1454; A61M 5/14546; A61M 5/14566; A61M 5/2033; A61M 5/31576; A61M 5/31578; A61M 2005/2411
See application file for complete search history.

(56) References Cited

U.S. PATENT DOCUMENTS

| | | | |
|---|---|---|---|
| 1,770,633 A * | 7/1930 | Smith | A61M 5/24 604/234 |
| 3,543,603 A | 1/1970 | Gley | |
| 4,381,005 A | 4/1983 | Bujan | |
| 5,788,673 A * | 8/1998 | Young | A61M 5/14526 604/131 |
| 6,358,239 B1 * | 3/2002 | Rake | A61M 5/148 128/DIG. 12 |
| 2010/0004638 A1 * | 1/2010 | Gibson | A61M 5/14276 604/891.1 |

OTHER PUBLICATIONS

PCT International Search Report and Written Opinion dated Jan. 11, 2013 pertaining to International application No. PCT/EP2012/053293.

* cited by examiner

*Primary Examiner* — Manuel A Mendez
*Assistant Examiner* — Justun L Zamory
(74) *Attorney, Agent, or Firm* — Dinsmore & Shohl, LLP

(57) ABSTRACT

A spring force assembly for biasing a displaceable stopper of a liquid medicament cartridge including a spring element arranged along a longitudinal axis, with brace elements and coupling elements, with the coupling elements restricting the distance between the brace elements which also restricts the possible expansion of the spring element.

9 Claims, 9 Drawing Sheets

FIG. 1

Prior Art

SPRING FORCE ASSEMBLY FOR BIASING OR ACTUATING STOPPERS OF SYRINGES, INJECTION PEN CARTRIDGES AND THE LIKE

CROSS-REFERENCE TO RELATED APPLICATIONS

The present application is a continuation of International Application No. PCT/EP2012/053293, filed Feb. 27, 2012, which is hereby incorporated by reference in its entirety.

FIELD OF TECHNOLOGY

This application relates to spring force assemblies for biasing or actuating stoppers of syringes, injection pen cartridges and the like, infusion pump devices with spring force units for biasing or actuating stoppers, and the methods of use of such spring force assemblies.

BACKGROUND

Insulin infusion pumps and insulin injection pens are useful devices in the treatment of diabetes mellitus, since they allow controlled parenteral administration of highly potent insulin solution by the patient himself, in variable but exactly measured doses, as required by the momentary physiological need of a patient. Similar devices are also useful for the treatment of other medical conditions, such as e.g. pain treatment.

Common insulin pump devices and insulin injection pens directly obtain the administered dose of liquid medicine from a disposable reservoir container in the form of a cylindrical cartridge or ampoule. For connecting the container with the downstream fluidic system, the proximal end of the container is provided with a pierceable membrane or another fluidic connector, e.g. a male luer connector. The other, distal end of the container is provided with a displaceable stopper that sealingly closes the inner container volume. The liquid is conveyed similar to a syringe, by actuating and unidirectionally displacing the stopper toward the proximal end. The dosed volume of liquid medicine depends on the cross-sectional area of the container and the displacement of the stopper. The stopper is actuated manually or spring force driven, in the case on an injection pen, or by a motor unit, operationally coupled to the stopper for example by a rod, in the case of a infusion pump. The displaceable container can be provided prefilled with liquid medicament, or empty, to be filled by the user from a larger container such as e.g. a standard vial with 10 ml volume.

For cost and hygiene reasons, Infusion pump devices are advantageously divided into one or more reusable parts, and one or more disposable parts, the latter being generally the parts that come into contact with the fluids to be administered.

In an advanced design of infusion pump devices, a separate dedicated dosing unit is arranged downstream of the liquid medicament reservoir, and retrieving the liquid medicament from the upstream reservoir and conveying it downstream toward the injection site. Such a dosing unit can for example be realized with a micro membrane pump or a micro piston pump, which are especially designed for precise metering of small volumes. While several designs for such dosing units are known in the art, they are rather complex, expensive and critical with respect to large scale manufacture. An advantageous dosing unit is disclosed e.g. in EP 2163273 A1, in which a piston pump with a comparably small volume is fluidly connected to a larger up-stream primary reservoir and a downstream injection site by a three-way valve. With a filled pump cylinder, the dosing unit can deliver several exactly measured doses of variable size. When the pump cylinder is empty, it is refilled in one stroke from the primary reservoir.

When a rigid cartridge with displaceable stopper is used a the primary reservoir, for example a prefilled injection pen cartridge with 3 ml volume, sucking liquid from the primary reservoir with the piston pump will produce a negative pressure in the cartridge and the upstream fluidic system. However, the force resulting from the achievable pressure differential over the displaceable stopper will typically be too small to overcome the sticking friction force between stopper and cartridge wall. Said sticking force may have a typical value of approx. 15 N, but may widely vary between 0 and 30 N, since for the intended use for which such cartridges or ampoules are produced, the sticking force does not play a role. For this intended use, the stopper is mechanically actuated from the back, and the necessary force can be overcome by the mechanical actuation in the injection pen, or an actuation unit such as a spindle drive of a syringe type infusion pump device.

To be able to use rigid cartridges with displaceable stoppers for downstream dosing type infusion pumps, the displaceable stopper has to be biased, in order to overcome friction between stopper and container wall. This has been achieved in the prior art by placing a compression spring at the distal end (opposite to the outlet) of the cartridge behind the displaceable stopper, exerting a bias force on the stopper. Such a spring must exert a force that is larger than the upper end of the statistical varying sticking force of cartridges of a certain type, over the complete range of stopper movement. Thus for a sticking force up to 30 N, the spring force must be over 30 N, which for the small dimension of an infusion pump requires comparably strong compression springs.

If a downstream dosing unit allows the generation of a fluidic suction pressure, the biasing force may be chosen smaller. However, since the fluidic suction pressure that can be exerted by a dosing unit cannot exceed atmospheric pressure, some spring biasing is typically required also for such a design.

Figure 1:
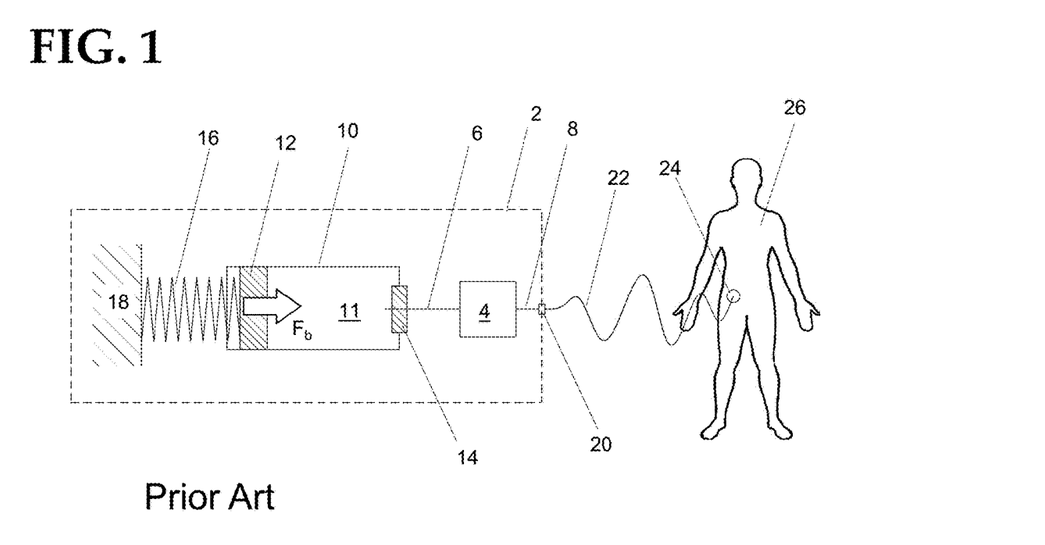
FIG. 1 schematically shows an infusion pump device as it is known from the prior art, with a downstream dosing unit for dosing the liquid medicament, a rigid container with displaceable stopper as the primary reservoir, and a compression spring for biasing the primary reservoir.

FIG. 1 schematically depicts such a prior art infusion pump device 2. A rigid cartridge 10 comprises a pierceable septum 14, across which a hollow cannula is arranged, fluidly connecting the inner volume 11 of the cartridge with an upstream fluidic system 6 of the pump device. A dosing unit 4 receives liquid medicament from the cartridge, and conveys said liquid medicament in small doses via infusion tubing 22 and injection site 24 into the body tissue of the patient. A compression spring 16 arranged between the casing structure 18 and the stopper 12 subjects said stopper to a bias force $F_b$ along the longitudinal axis of the cartridge. The applied spring force has to be chosen such that during the complete possible range of stopper motion the sticking friction force of the stopper is overcome, resulting in an overpressure in the inner volume 11 of the cartridge 10, and generating a positive pressure differential in the cartridge. Due to the positive pressure the dosing unit 4 can obtain liquid from the reservoir 10 with minimum energy need. At the same time the pressure differential should not be too large, since this could be detrimental in view of upstream leakage. Advantageously long springs should be used that are strongly compressed, thereby achieving a more constant spring force when the spring expands during the emptying of the cartridge.

Compression springs tend to kink and buckle to the side, an effect that depends on the outer spring diameter, the diameter of the spring rod, the spring constant, the length, etc. Thus such springs are prone to getting caught, particularly when they are applied in reusable units, and thus have to be recompressed when an emptied cartridge is replaced.

Incorrectly recompressed springs may become damaged, or may fail, thereby potentially causing dosing errors caused by incomplete refilling of the dosing unit, or by aspiration of gas bubbles resulting from underpressure in the cartridge.

In addition, such recompression can be a difficult manual task, particularly when long springs are used, or for patients that have impaired fine motor skills.

The mounting of a long compression spring into an infusion pump device is complicated and difficult to automatize, which increases the manufacturing costs.

There is a general need for improvement in this area.

Embodiments described herein provide for an advantageous spring force assembly that improves the state of the art with respect to the above-mentioned and other problems. Such a spring force assembly reliably functions after a large number of recompression cycles, and provides a spring force that varies only in a small bandwidth during expansion. Embodiments described herein provide for a spring force assembly that is unsusceptible to buckling and kinking, has a small number of parts that can be easily assembled, and is producible at a low cost. The assembly spring force assembly is easy to mount in an infusion pump device. These and other long-felt needs in the art are substantially achieved by embodiments described herein.

SUMMARY OF THE INVENTION

The present invention may comprise one or more of the features recited in the attached claims, and/or one or more of the following features and combinations thereof.

Specific embodiments described herein provide for a spring force assembly for biasing a displaceable stopper of a liquid medicament cartridge, comprising a spring element arranged along a longitudinal axis, comprising: a first brace element arranged on one longitudinal end of the spring element; a second brace element arranged on the other longitudinal end of the spring element; a first coupling element attached to the first brace element and aligned to the longitudinal axis; and a second coupling element attached to the second brace element and aligned to the longitudinal axis; and wherein the first coupling element and the second coupling element are operationally coupled to each other in such a way that they restrict the distance between the first brace element and the second brace element to a certain maximum value, thereby also restricting the possible expansion of the spring element.

Additional specific embodiments described herein provide for an infusion pump device, comprising a spring force unit for biasing a displaceable stopper of a liquid medicine cartridge.

Yet more specific embodiments described herein provide for a method for biasing a displaceable stopper of a liquid container or a syringe comprising: providing: a spring force assembly comprising: a spring element arranged along a longitudinal axis, comprising: a first brace element arranged on one longitudinal end of the spring element; a second brace element arranged on the other longitudinal end of the spring element; a first coupling element attached to the first brace element and aligned to the longitudinal axis; and a second coupling element attached to the second brace element and aligned to the longitudinal axis; and wherein the first coupling element and the second coupling element are operationally coupled to each other in such a way that they restrict the distance between the first brace element and the second brace element to a certain maximum value, thereby also restricting the possible expansion of the spring element; and biasing the displaceable stopper of the liquid container or the syringe with the spring force assembly.

BRIEF DESCRIPTION OF THE DRAWINGS

In order to facilitate a fuller understanding of the present disclosure, reference is now made to the appended drawings. These references should not be construed as limiting the present disclosure, but are intended to be exemplary only.

DESCRIPTION OF EMBODIMENTS OF THE INVENTION

Figure 2:
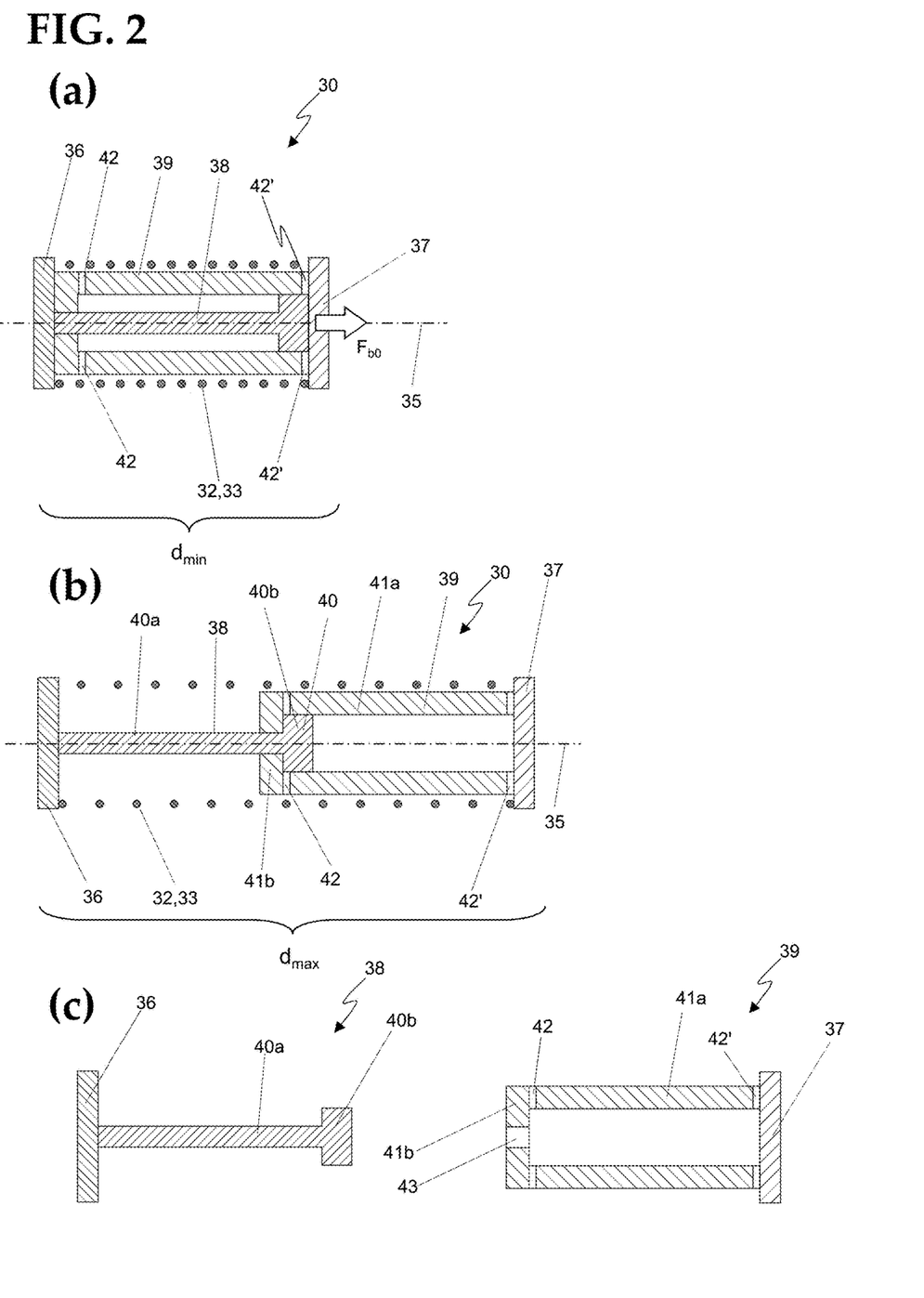
FIG. 2 schematically shows a longitudinal section of an advantageous embodiment of a spring force assembly according to the disclosure, (a) in the compressed state, (b) in the expanded state, and (c) in a disassembled state.

A first embodiment of a spring force assembly 30 according to the disclosure is schematically shown in FIG. 2. The assembly is intended to be mounted in an infusion pump device and to be operationally coupled to a liquid medicament cartridge.

Two brace elements 36, 37 are arranged on the longitudinal ends of a spring element 32 in the form of a helical compression spring 33. The brace elements are designed in such a way that they can support the spring element 32 arranged between them. In the shown embodiment the brace elements are realized as disks with a diameter that is larger than the outer diameter of the helical spring.

The assembly has two coupling elements interacting in the form of a telescope, arranged inside the spring element. A first coupling element 38 comprises a shaft 40a, which is attached on one end to a first 36 of said brace elements, and on the other end to a disk 40b. A second coupling element 39 comprises a tube element 41a, which is attached on one end to the second 37 of said two brace elements. On the other end of the tube element 41a a circumferential shoulder 41b protrudes inwards, leaving open a central bore 43.

In the assembled state, the first coupling element 38, the spring element 32, and the second coupling element 39 are aligned along a longitudinal axis 35. The coupling elements are arranged inside the spring element. The shaft 40a is arranged in the central bore 43, and the disk 40b is located in the inner volume of the tube element 41a. Thus the coupling elements 38, 39 are positively locked to each other, while being shiftably displaceable to each other along the longitudinal axis 35. Essentially they interact like the tubular parts of a telescope. Since the first and second brace elements 36, 37 are connected to the corresponding first and second coupling elements 38, 39, they positively lock the spring element 32 along the longitudinal axis, while the coupling elements positively lock the spring element perpendicular to the axis.

The length of the spring force assembly 30 can vary between a minimum length $d_{min}$, where either the disk 40b of the first coupling element 38 and/or the shoulder 41b of the second coupling element 39 abut the opposite brace element, and a maximum length $d_{min}$, where the disk 41b abuts the protruding shoulder 41b. Thus a spring force assembly 30 according to the disclosure has a maximum expansion state (FIG. 2(b)) and a maximum compression state (FIG. 2(a)). Advantageously the dimensions of the helical spring 33 are chosen such that its length in an unloaded state is considerably longer than the maximum expansion length $d_{max}$, and the maximum possible compression length should be smaller than the maximum compression length $d_{min}$. The advantageous result is a slower decrease of the spring force exerted by the spring element, from $F_{b0}$ at the maximum compressed state to $F_{b1}$, just before reaching the maximum expanded state, at which the expansion will stop and the spring force will drop to 0. A generally short length of the spring force assembly is generally favorable, since the length of the spring force assembly typically contributes significantly to the overall length of the infusion pump device.

In a spring force assembly according to the disclosure, very long compression springs can be used, which would else be very difficult to handle for a user when recompressing a prior art spring. Since the spring element is guided and supported radially by the coupling elements, it can only buckle and kink outwards within a small play. A user can easily recompress the expanded spring force assembly. Furthermore in the assembled state the spring force element is a compact unit, also in the expanded state, and can be efficiently handled during the manufacturing process of an infusion pump device according to the disclosure. This characteristic is favorable both for embodiments where the spring force assembly is reusable and needs to be recompressed by the user, and for embodiments where the spring force assembly is a single-use disposable.

In the given embodiment, the tube element is provided with venting bores 42, 42', for pressure relief of the volumes enclosed by the tube element and the disk. In advantageous embodiments of spring force assemblies according to the disclosure, the venting bores, the tube element and the disk may interact together as a damper, allowing only a certain maximum displacement velocity during expansion, due to the counter force caused by the overpressure and underpressure on the proximal and distal side of the disk. The exerted spring force is not impaired, since during normal operation the expansion velocity will be very slow. Such a design avoids possible injuries and damages caused by uncontrolled expanding springs, for example when a user slips off when manually recompressing the spring force assembly. Furthermore such a damping mechanism allows in certain applications, where the spring force assembly in its maximum compressed state does not yet have contact with the stopper, to drive the spring force assembly in a controlled manner from the maximum compressed state to a start point, where it contacts the stopper.

In a further variant, one or more of said venting bores can be equipped with a one-way valve, in order to achieve a damping effect during expansion, but not during compression.

Another possibility to realize a damping mechanism is friction between the coupling elements, and/or friction between coupling elements and spring element.

Figure 3:
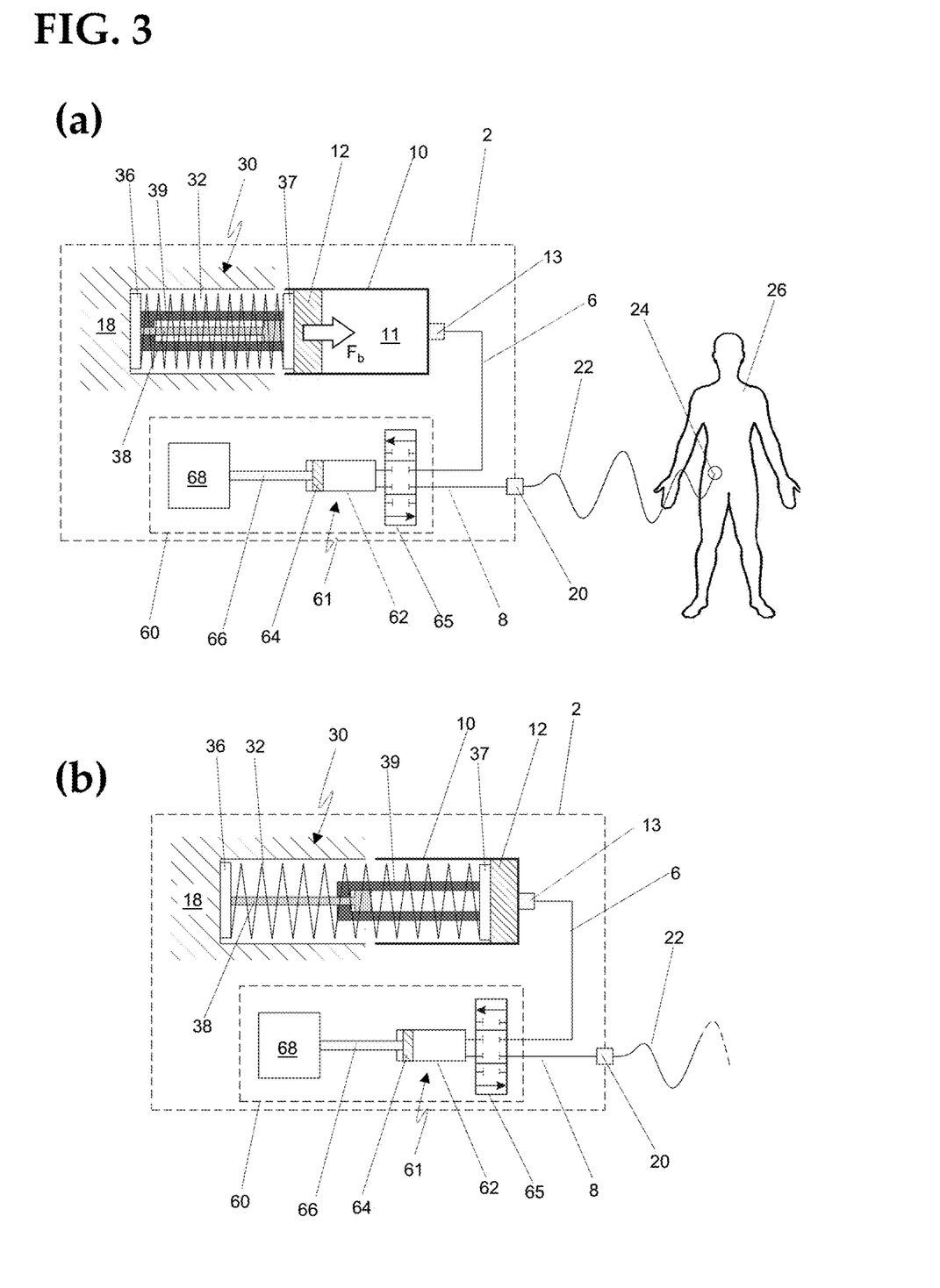
FIG. 3 schematically shows an infusion pump device according to the disclosure, in which a primary reservoir cartridge is biased with a spring force assembly according to the disclosure similar to the one in FIG. 2(a) with full cartridge and compressed spring force assembly, and (b) with empty cartridge and expanded spring force assembly.

If the different elements are adjusted accordingly, a damping mechanism can also be used to control the sequence in which three or more coupling members start to move, for example by providing a damping effect only between two of three coupling elements. As a result, the two damped coupling elements will start to displace in regard to each later A spring force assembly 30 similar to the spring force assembly 30 discussed above is schematically shown in FIG. 3(a) as a part of an infusion pump device 2 according to the disclosure. The infusion pump device 2 comprises a downstream dosing unit 60 and a filled liquid medicament reservoir in the form of a rigid cartridge 10. The reservoir volume 11 of the rigid cartridge is fluidly connected to the dosing unit 60 via fluidic connector 13 and upstream fluidic system 6. The dosing unit is fluidly connected 8 to a connector 20, which can be releasably connected to external infusion tubing 20 and injection site 24. In order to exert a bias force $F_b$ on the displaceable stopper 12, a compressed spring force assembly 30 according to the disclosure is arranged between a casing structure 18 and the displaceable stopper 12.

The dosing unit 60 comprises a piston pump 61 with cylinder 62 and piston 64. The piston is operationally coupled to an actuation unit 68, e.g. by a piston rod 66 as in the given example. The piston pump can be alternatingly connected by a ¾-way valve 65 either to the reservoir 10, for refilling the pump cylinder 62, or to the downstream fluidic system 8, for administering a multitude of exactly metered liquid medicine doses. Additional necessary or optional parts of such an infusions pump device, such as bubble filter, occlusion detector, control unit etc. have been omitted for simplicity, since they are not directly relevant for the disclosure.

For refilling the emptied pump cylinder, the valve 65 is actuated such that the pump cylinder is fluidly connected to cartridge 10. The actuation unit 68 then retracts the piston, sucking in liquid medicament from reservoir volume 11. Since the bias force of the spring force assembly 30 overcomes the sticking friction between stopper 12 and cartridge wall, it causes certain over pressure in the inner volume 11. Thus, for retrieving liquid from the cartridge, the actuation unit 68 does only need to apply a minimal force when retracting the piston 64.

After several refilling and administration cycles, the primary reservoir 10 will be empty, as shown in FIG. 3(b). The spring force assembly is now partially located inside the distal end of the rigid cartridge 10. To ensure a complete drain of the cartridge, without wasting expensive liquid medicine such as insulin solution, the maximum expansion length of a spring force assembly should be adapted such that the maximum expansion is not reached before the stopper 12 reaches the stop, thereby ensuring ongoing bias pressure until complete drain of the cartridge is achieved.

As can be seen, in the expanded state the brace element 37 and part of the spring element 32 will be located inside the disposable cartridge cylinder. As a consequence, in a spring force assembly according to the disclosure the diameters of the spring and the second brace element have to be adapted to the dimensions of the type of cartridge to be used.

The spring force assembly according to the disclosure as shown in FIG. 3(b) differs from the previously discussed embodiment in that the two coupling elements 38 (dark grey) and 39 (light gray) have a diameter that is considerably smaller than the spring element, and thus cannot support the spring element in the radial direction. To avoid buckling and kinking of the strongly compressed spring element, the spring force assembly is arranged in a cylinder-shaped recess of the casing structure 18. As a result, in this particular embodiment the spring is supported and guided by the walls of the recess and the inner wall of the cartridge structure.

Figure 4:
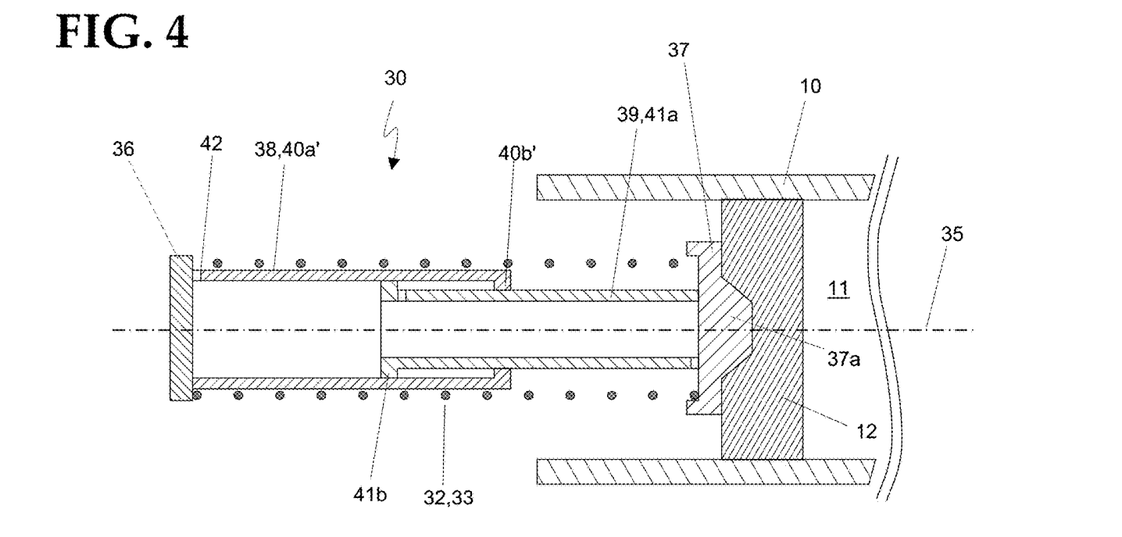
FIG. 4 schematically shows a longitudinal section of another embodiment of a spring force assembly according to the disclosure, with both coupling elements realized as tube elements, the spring force assembly being in an intermediate, partially expanded state.

A variant of a spring force assembly according to the disclosure is schematically depicted in FIG. 4. The assembly 30, being partially expanded, is arranged between a rigid cartridge 10 on one longitudinal end and a structure of the pump casing (not shown) on the other end. The first coupling element 38 is realized as a tube element 40a' with a circumferential shoulder 40b' on one end. In the extended state said shoulder abuts the protruding shoulder 41b of the second coupling element 39.

The brace element 37 of the spring force assembly 30 facing the displaceable stopper 12 in the rigid cartridge 10 has the shape of a truncated cone 37a. It interacts with a corresponding depression in the distal surface of the stopper. An advantage of such an embodiment is a stable alignment of the stopper and the spring force assembly, also if the spring force assembly has an outer diameter that is smaller than the diameter of the stopper.

Figure 5:
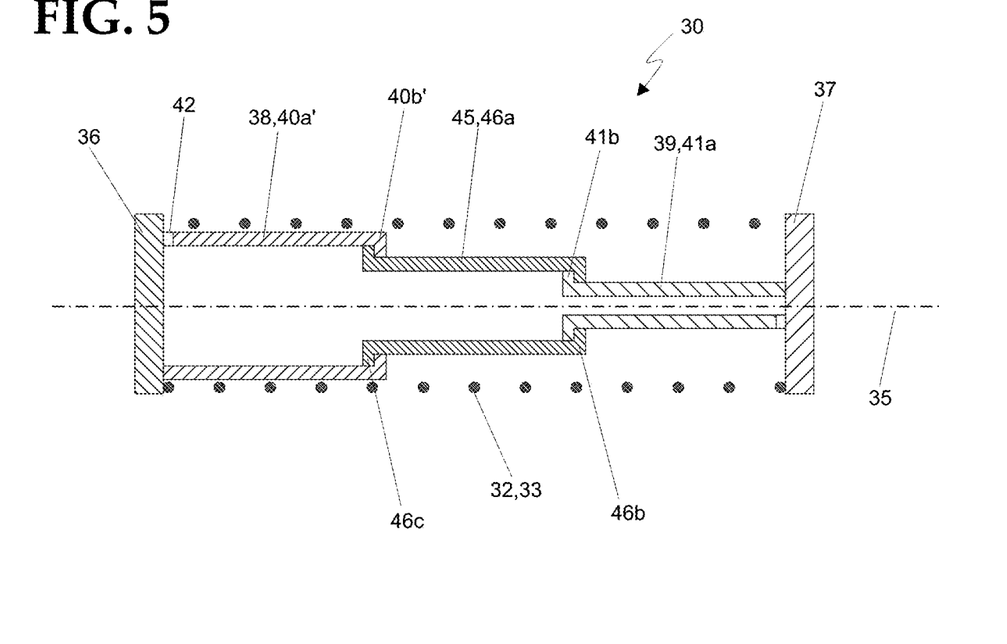
FIG. 5 schematically shows a longitudinal section of a further embodiment of a spring force assembly, having three coupling elements, in the maximum expanded state.

In the spring force assemblies discussed so far, the length of the assembly in the expanded state was approximately twice the length in the compressed state. For more compact spring force assemblies according to the disclosure, additional intermediate coupling elements can be used. Such an advantageous embodiment variant is shown in FIG. 5, in the maximum expanded state. Both the first coupling element 38 and the second coupling element 39 are realized as tube elements with protruding shoulders 40b', 41b. Aligned to the longitudinal axis 35, a third, intermediate coupling element 45 in the form of a tube element 46a is arranged, having a first circumferential shoulder 46b protruding inwards, and engaging behind the protruding shoulder 40b' of the first coupling element 38, and a second circumferential shoulder 46c protruding outwards, engaging behind the protruding shoulder 41b of the second coupling element. Thus intermediate coupling element 45 operationally couples the first and second coupling elements 38, 39. In the expanded state, the length of the spring force assembly is approximately three times the length in the compressed state.

Figure 6:
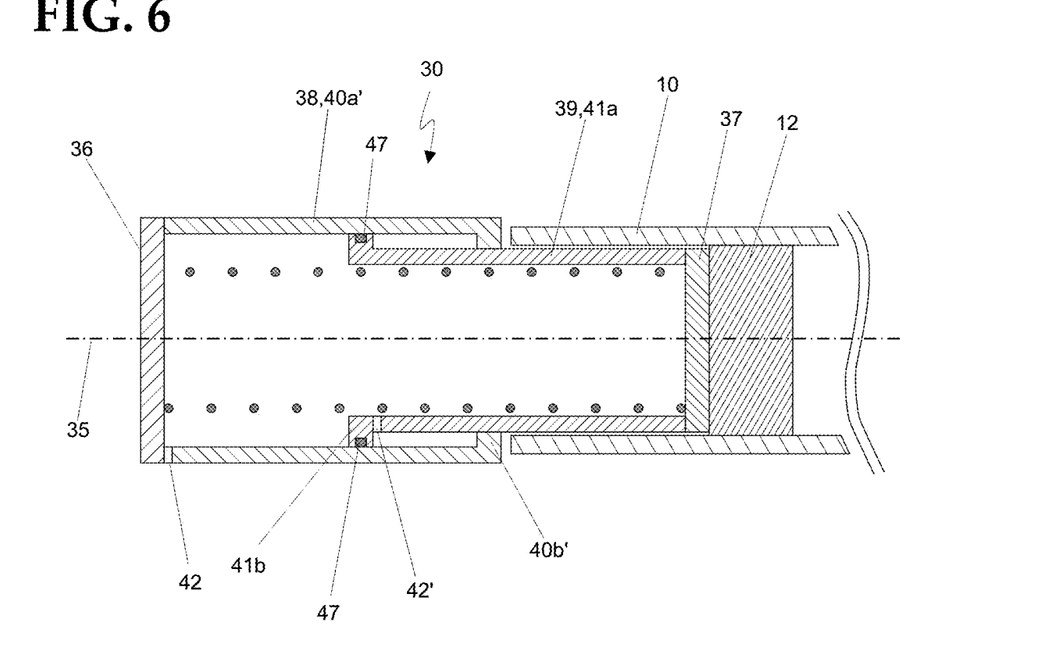
FIG. 6 schematically shows a longitudinal section of another advantageous embodiment of a spring force assembly according to the disclosure, with the helical spring arranged inside the coupling elements, in an intermediate, partially expanded state.

In the examples of the disclosure given so far, the coupling elements have been arranged inside the spring element. However, it is also possible to arrange the spring element inside the coupling elements. FIG. 6 schematically shows such an advantageous embodiment, arranged between an infusion pump structure (not shown) and a rigid cartridge.

The coupling elements 38, 39 are realized as tube elements 40a, 41a, with protruding shoulders 40b', 41b that engage with each other. The spring element 32 in the form of a helical compression spring is arranged inside the tube elements. Such a particular variant of an advantageous assembly has the advantage that the spring is not accessible from outside. As can be seen, in the given example it is sufficient if the outer diameter of the second coupling element 39 is smaller than the inner diameter of the cartridge 10.

In the given example, an O-ring seal 47 is arranged in a recess on shoulder 41b, sealingly closing the inner volume enclosed by the coupling elements. This allows increasing the damping effect due to the volume change during expansion. The bore 42 can be chosen as small as necessary, without any air leaking between the two coupling elements. Such O-ring seals can also be applied for the other embodiments discussed so far that have a dampening effect.

In an advantageous variant of such a spring force assembly according to the disclosure, one of the coupling elements can be provided with a protruding structure on its outer surface, for example a ring, that will be sheared off when reaching the distal edge of the cartridge, thereby slowing down expansion of the spring force assembly before the brace element reaches the stopper. If the coupling elements are arranged inside the spring element, a brace element may be provided with such a structure.

Figure 7:
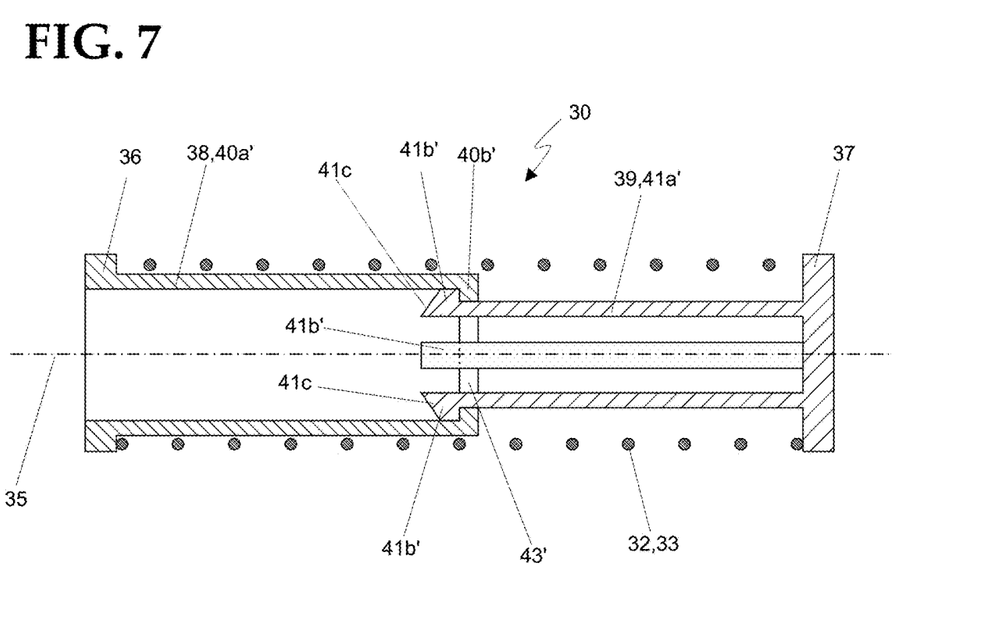
FIG. 7 schematically shows a longitudinal section of a further advantageous embodiment of a spring force assembly according to the disclosure, which can be assembled using a locking mechanism, in the expanded state.

In an advantageous embodiment of the disclosure that has only three components, shown in FIG. 7, corresponding brace elements and coupling elements are formed as one single part, which reduces manufacturing and assembly costs, and is particularly suitable for injection molded parts. The first coupling element 38 is realized as a tube element 40a' with protruding shoulder 40b', integrally molded to a brace element in the form of a flange 36. Since such a component has no undercut parts, it can be easily manufactured by injection molding. In the second coupling element 39, the tube element is reduced to four parallel, slightly flexible beams 41a' (of the four beams one is shown from the side, and two in a cross-section) arranged along a circumference of the brace element 37. The protrusions 41b' of the beams 41a' are provided with ramps 41c. This component has also no undercuts and can be produced by injection molding.

For assembling the spring force assembly, the coupling elements 38, 39 are inserted into the two ends of the spring element 32. The two brace elements 36, 37 are then pressed together, thereby compressing the spring 32. When the ramps 41c of the beams 41a' of second coupling element 39 reach the protruding shoulder 40b of coupling element 38, the beams 41a' and protrusions 41b' are deflected inwards. After having passed the central bore 43' of the protruding shoulder 40b, the deflected beams snap back, and the protrusions 41b' engage behind the protruding shoulder 40b, positively locking the two coupling elements together. The spring force assembly 30 according to the disclosure is completely assembled, as shown in FIG. 7, and ready for use.

In the exemplary embodiments discussed so far, the spring force assembly has been realized as a separate unit. In alternative embodiments of the disclosure, it is also possible to temporarily or permanently fasten the first brace element to the pump structure, or using the structure itself as the brace element supporting the spring element. Such a variant can be useful for spring force assemblies that are intended to be reusable.

Analogously it is also possible to temporarily or permanently attach the second brace element to the displaceable stopper of a cartridge. Such an approach can be used for disposable spring force assembly/cartridge combinations, where empty or prefilled cartridges are provided with an integrated spring force assembly. Advantageously, the parameters of such a spring force assembly (dimensions, spring force, etc) are adapted to the specific type of cartridge it is used for.

Figure 8:
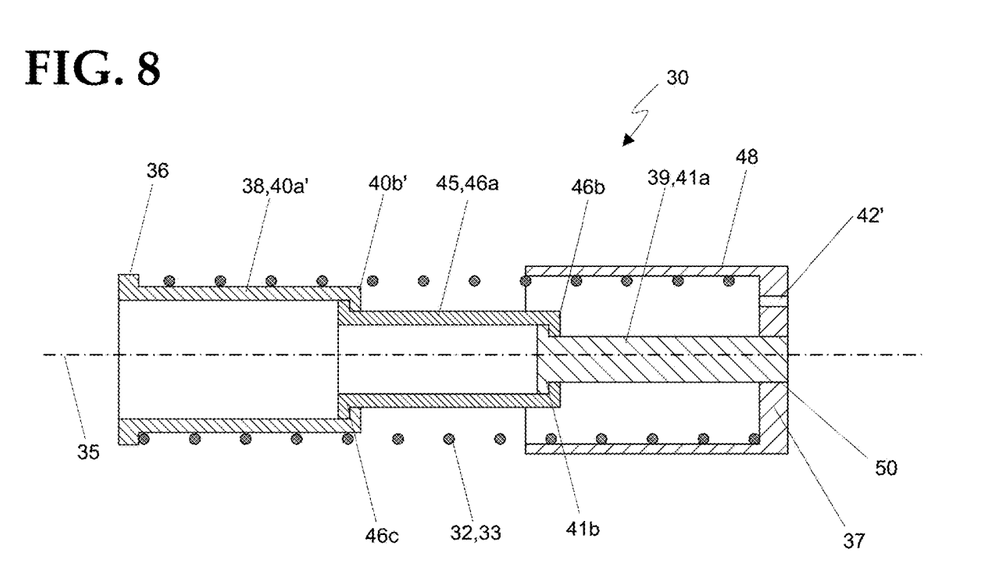
FIG. 8 schematically shows a longitudinal section of yet another advantageous embodiment of a spring force assembly according to the disclosure, with an outer sleeve.

Another advantageous embodiment of a spring force assembly according to the disclosure is shown in FIG. 8, in the expanded state. The assembly comprises three coupling elements 38, 39, 45. The first brace element 36 is realized as a flange on the distal end of the first coupling element 38. The second brace element 37 is provided with a sleeve 48 that covers part of the spring element 22. The second coupling element 39 is connected with the second brace element 37 with a screw joint 50. The length of the sleeve 48 is chosen such that in the maximum compressed state the sleeve 48 covers the complete spring element. The shown embodiment is assembled by inserting the coupling elements 39, 45, 38 and the spring element 22 into each other, and finally screwing together coupling element 39 and second brace 37, thereby positively locking the different parts to each other.

One advantage of such an embodiment is the protection of the spring element in the compressed state. Furthermore the sleeve can be used to guide the spring force assembly within the cartridge. Yet another advantage of sleeve 48 is the radial support it provides in the expanded state to the spring element 22 in the proximal region of the spring force assembly.

Such an embodiment of the disclosure is also useful for implementing a damping mechanism based on friction, as it has been discussed further above, since the radial surface frictionally interacting with the spring element is increased. The spring is frictionally coupled both to the outer cylindrical surface of the first coupling element 38 and the inner cylindrical surface of the sleeve 48.

Figure 9:
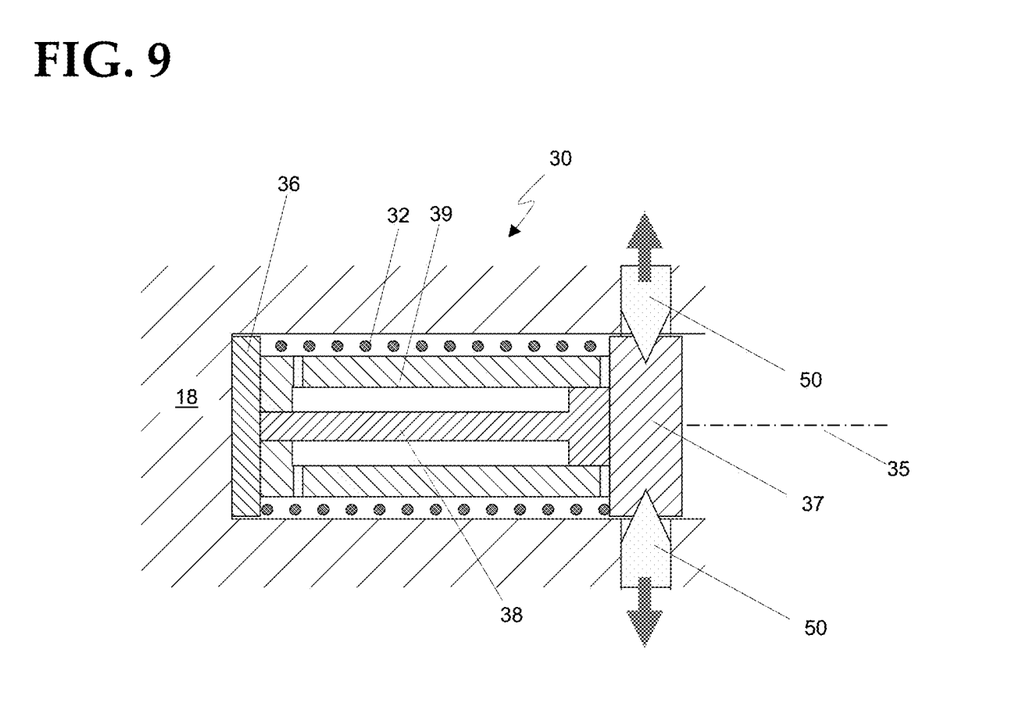
FIG. 9 schematically shows a longitudinal section of an advantageous embodiment of a spring force assembly according to the disclosure arranged in a cavity of the pump device, with a locking mechanism for releasably locking the spring force assembly in a compressed state.

In yet another advantageous embodiment of a spring force assembly according to the disclosure, a locking mechanism is provided, which allows to releasably locking the spring force assembly in a compressed state. Such a variant of a spring force assembly is shown in FIG. 9, where a spring force assembly 30 similar to the one in FIG. 2 is arranged in a cylindrical cavity in the casing structure 18 of an infusion pump device. One brace element 36 of the compressed spring force assembly is supported by the longitudinal end of the cavity. The other brace element 37 is positively locked by two locking elements 50 in the form of wedges. The spring force assembly is locked in the compressed state.

Said wedges can be retracted perpendicular to the longitudinal axis, thereby unclamping the brace element 37, and releasing the second coupling element. The spring force assembly can now expand, or exert a spring force, respectively.

The shown advantageous embodiment provides the possibility to have the spring force assembly in the compressed state when inserting a new cartridge into the infusion pump device, without the need of manually holding back the spring force assembly, which may be difficult for a user if the spring force is high. For releasing the locking mechanism, the wedges are retracted, for example by a user actuating a release button or the like.

Any suitable mechanism may be used for releasably locking the spring force assembly in the compressed state. Instead of positively locking the brace element facing the cartridge, as in the shown example, it can be locked force-fit, for example by suitable camping elements. Other possibilities include for example a bayonet lock, or a lock that can be released by mechanically deforming parts of the spring force assembly.

Alternatively to locking the brace element 37, the corresponding coupling element 39 can be locked in the position of the compressed state, for example by gripping the distal end of the coupling element 39 with suitable clamping elements.

Yet another possibility to lock the spring force assembly in the compressed state is to restrain the brace element 37 and/or the coupling element 39 by magnetic force, for example with an electromagnet that temporarily locks a ferromagnetic part of the spring force assembly.

The discussed locking of a spring force assembly according to the disclosure is also applicable for biasing spring elements without coupling elements, as they are known from prior art infusion pumps.

In advantageous infusion pump devices as they have been discussed, the fluidic connection between the upstream fluidic system and a newly inserted liquid medicament cartridge can be established in different ways.

In one approach, in a first step a new, prefilled cartridge is inserted by a user into a corresponding cavity or holding structure of the pump casing. A hollow needle fluidly connected to the upstream fluidic system and aligned to the cartridge axis is provided. For connecting the cartridge, the user pushes the cartridge toward the needle, which eventually penetrates the pierceable membrane or septum on the proximal end of the cartridge. Fluidic connection is established. In a second step the displaceable stopper of the cartridge is biased by a spring element, e.g. a spring force assembly according to the disclosure. In a particularly advantageous variant the spring element or spring force assembly is provided locked in the compressed state, or in a partially expanded, intermediate state, just before reaching the stopper. After fluidic connection has been established, locking is released, and the stopper is biased, thereby exerting a pressure on the content of the cartridge.

In another advantageous approach, again a spring element or a spring force assembly according to the disclosure is locked in the compressed state, or in a partially expanded, intermediate state, just before reaching the stopper. A new, prefilled cartridge is inserted by a user in the corresponding cavity of the casing structure, while the connector element in the form of a pierceable membrane or septum remains unpierced. Upon release of the locked spring force assembly, the cartridge is linearly displaced towards the hollow needle, actuated by the expanding spring force assembly. The length of the hollow needle is chosen such that the needle will be driven completely through the pierceable membrane, thereby fluidly connecting the cartridge to the upstream system. When the cartridge reaches the end of the cavity and cannot displace further, the spring force assembly will exert a force on the stopper and will generate bias pressure in the cartridge. Thus with such an approach a proper fluidic connection is established before the content of the cartridge is actually subject to overpressure, thereby avoiding leakage during the connection process.

In yet another advantageous variant, the hollow needle is realized as a displaceable element. In a first step, the cartridge is inserted into the cavity or holding structure. The pierceable membrane or septum remains unpierced. A spring element or spring force assembly according to the disclosure is provided, biasing the displaceable stopper of the cartridge. In a second step the hollow needle is displaced toward the septum, along the axis of the cartridge, and penetrates the septum. Fluidic connection is established. Such actuation of the hollow needle can be carried out by a user, e.g. by pressing a button or the like that is operationally coupled to the needle. In another approach the needle is spring biased, and upon release the spring is pushed forward and penetrates the septum, driven by the spring force.

The previously discussed variants can also be combined. For example can a release mechanism of a spring biased hollow connector needle be combined with a release mechanism of a spring force assembly locked in the compressed state. This allows to exactly defining the time sequence in which fluidic connection is established and bias pressure are is generated (pressure before connection, connection before pressure, or both at the same time).

The actuation of the different elements, such as a spring force assembly locking/release mechanism and a needle mechanism, can be achieved mechanically, particularly by manual actuation of the elements, or electrically, or combined.

If a spring according to the disclosure is provided as a disposable unit or as part of a disposable unit, intended to be disposed after a single use, it is advantageous to provide the spring force assembly as a pre-compressed unit.

One possibility is to provide the compressed spring force assembly packed tightly wrapped in a package. For releasing the spring force assembly, the package is cut trough along a circumferential line.

In another variant, two coupling elements are provided, connected by predetermined breaking points, for example thin polymer bars, or the two coupling elements are attached to each other by adhesive tape wrapped along the circumference of the coupling elements.

If on the other hand the spring force assembly according to the disclosure, or a prior art bias spring element, is part of a reusable unit, it is advantageous to be able to easily recompress the spring force assembly 30 or bias spring without complicated handling.

Figure 10:
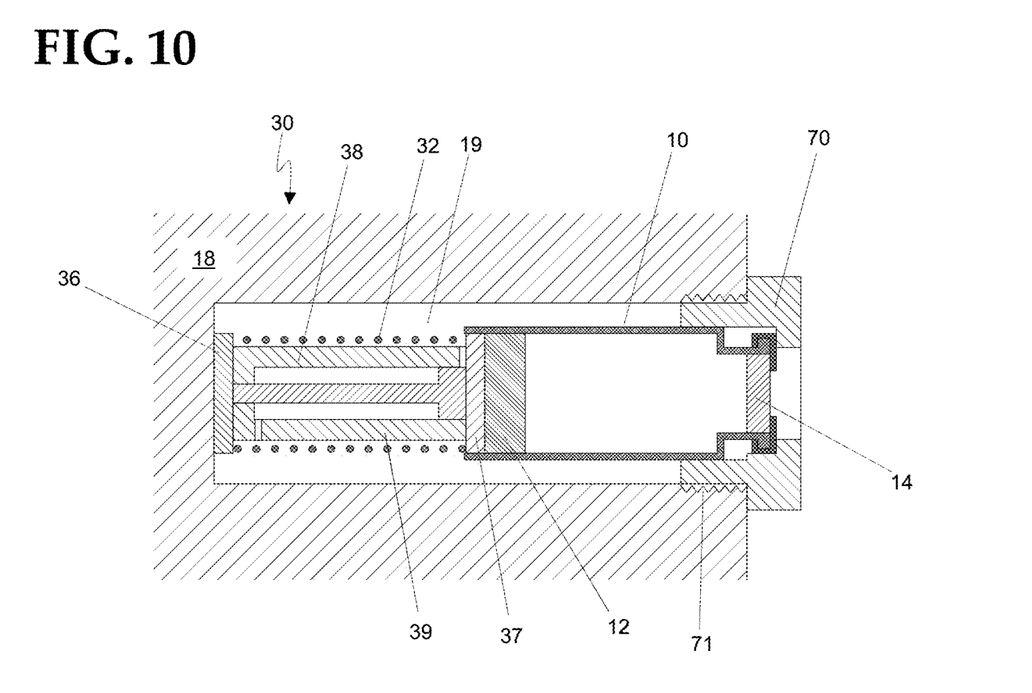
FIG. 10 schematically shows a longitudinal section of another advantageous embodiment of a spring force assembly according to the disclosure arranged in a cavity of the pump device, for manually compressing a spring force assembly while inserting a cartridge.

An advantageous embodiment of such a spring force assembly according to the disclosure that allows simple recompression is shown in FIG. 10. In this particular variant, a new cartridge 10, prefilled with the liquid to be administered, is pressed by a user into a cylindrical cavity 19 in the structure 18, thereby compressing a spring force assembly 30 according to the disclosure. The cartridge 10 is releasably locked in the cavity 19, for example with a threaded cap 70. The threaded cap 70 holds the proximal end of the cartridge 10 with the piercable septum 14, and is screwed into a corresponding thread 71 of the cylindrical cavity 19. Another variant could be a locking mechanism that fixates the cartridge in the cavity.

Since it is advantageous to avoid unnecessary contact with the pierceable membrane or septum of the cartridge, in order to minimize a risk of bacterial contamination during the penetration of the hollow needle of the upstream fluidic system through the septum, it is advantageous to temporarily cover the septum part of the cartridge during such manipulation, for example by a suitable cap or a seal that can be peeled off.

Figure 11:
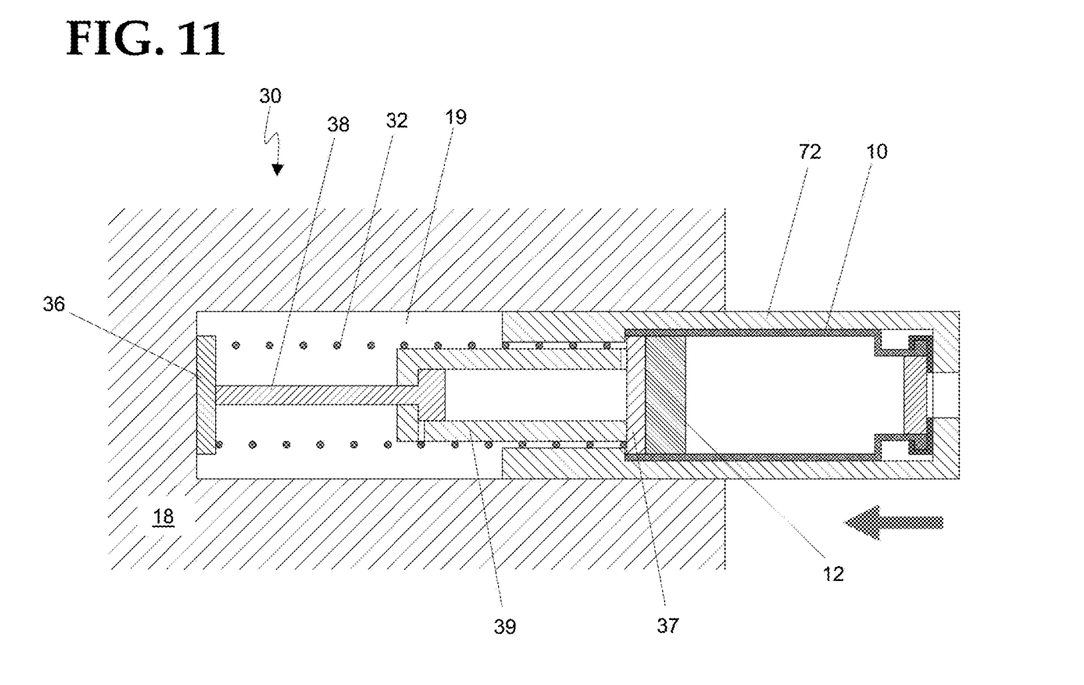
FIG. 11 schematically shows a longitudinal section of a further advantageous embodiment of a spring force assembly according to the disclosure arranged in a cavity of the pump device, with a cartridge holding block holding the both cartridge and the spring force assembly.

FIG. 11 discloses yet another advantageous variant of a spring force assembly according to the disclosure. An expanded spring force assembly 30 is mounted in a cartridge holding block 72. A prefilled cartridge 10 has been placed in the holding block 72, aligned to the spring force assembly. A part of the expanded spring force assembly protrudes through an opening in the body of the holding block. The block is inserted by the user into a cavity 19 of the pump structure 18, thereby compressing the spring force assembly. When eventually the block is locked in the cavity by a suitable releasable locking mechanism (not shown), the spring force assembly is operable.

Such an embodiment has the advantage that the handling is even more simplified. Only one single part has to be inserted into the pump. The pierceable membrane or septum of the cartridge cannot be touched by the user. In addition specific cartridge holding blocks can be provided for different types of cartridges, which allow a patient to use a variety of commercially available prefilled insulin cartridges, as well as cartridges filled by the patient himself, with one single infusion pump device. This gives the patient the possibility to choose the insulin medicament that is most suitable for him, and also the flexibility to change the medicament whenever necessary.

In the embodiment discussed above, the mechanical force is transmitted from the cartridge to the spring force assembly via the stopper and the liquid enclosed by cartridge wall and stopper. Thus the displaceable stopper of the cartridge is constantly subject to the spring force exerted by the spring force assembly.

Figure 12:
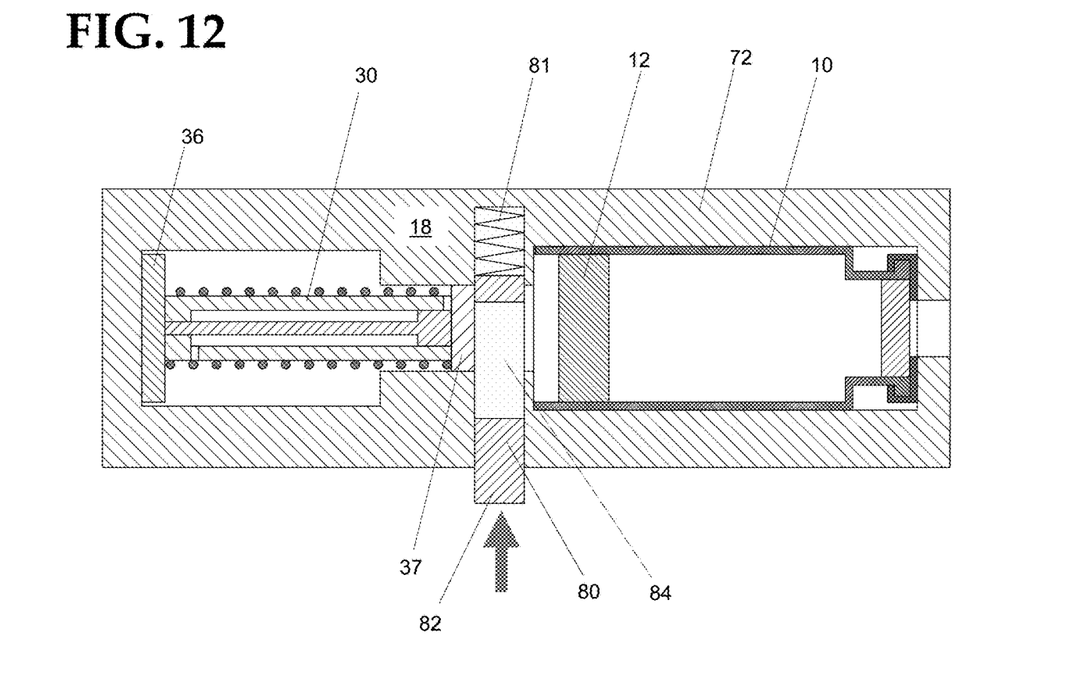
FIG. 12 schematically shows an advantageous cartridge holding block, provided with a release mechanism.

An advantageous embodiment of an infusion pump device according to the disclosure that does not bias the stopper unnecessarily early is depicted in FIG. 12. The spring force assembly 30 is mounted in a cartridge holding block 72 in the compressed state. A slidable gate element 80 is provided between spring force assembly and cartridge 30, locking the spring force assembly and preventing it from biasing the displaceable stopper 12 of the cartridge 10. The gate element 80 is provided with a spring element 81 that keeps the gate element in the locking position, and a cam 82 protruding from the block casing. When the block 72 is inserted by the user into the corresponding cavity of a pump, a ramp (not shown) provided in the cavity forces the cam 82 inwards when the block reaches a certain position. The gate element slides toward the biasing spring element 81. An opening 84 in the gate element 80 is shifted over the spring force assembly. The spring force assembly is released and expands toward the cartridge, advantageously slowed down by a suitable damper mechanism as it has been described above, and abuts and biases the stopper 12 of the cartridge. The spring force assembly is activated and operable.

Instead of a ramp another actuation mechanism can be used to push in the cam and to release the spring force assembly.

In the shown example the cartridge holding block comprises an opening that allows a hollow needle element to access a piercable membrane or septum of the cartridge. Alternatively the cartridge holding block can comprise means for fluidly connecting the cartridge to the upstream fluidic system of a dosing unit.

Figure 13:
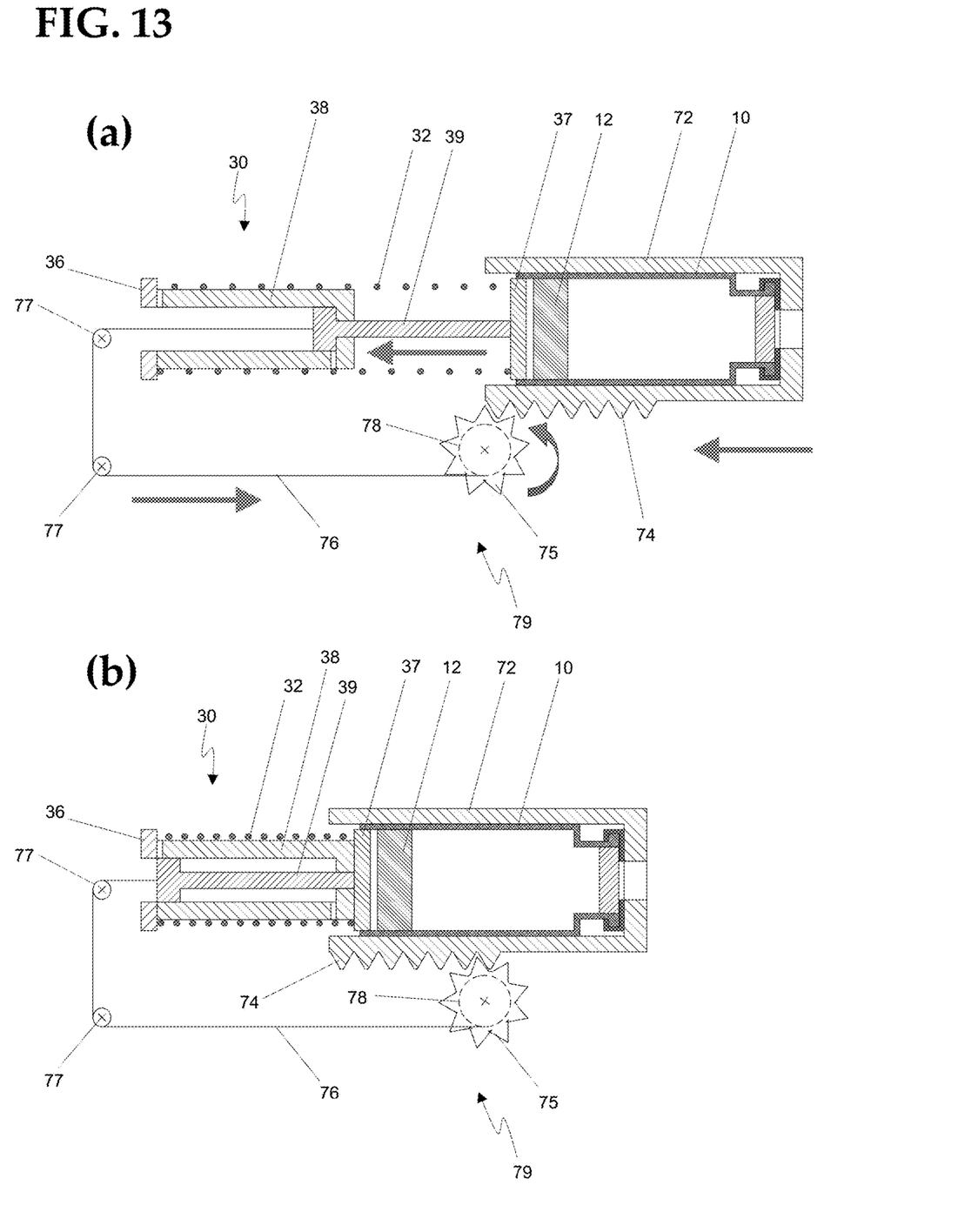
FIG. 13 schematically shows a longitudinal section of an advantageous mechanism in an infusion pump device according to the disclosure, for compressing a spring force assembly while inserting a cartridge, without biasing the displaceable stopper of the cartridge, (a) before the spring force assembly has been tensioned, and (b) after the spring force assembly has been tensioned.

A further advantageous embodiment of an infusion pump device according to the disclosure, which allows compressing a spring force assembly according to the disclosure, or another spring element, without biasing the displaceable stopper, is shown in FIG. 13.

The cartridge holding block 72 is provided with a cograil 74 along its longitudinal axis. When the block 72 is pushed into the corresponding cavity (not shown) of the pump device, said cograil 74 interacts with a cogwheel 75 provided in the pump structure, and rotates the cogwheel. The cogwheel 75 is coupled to a bobbin 78, which winds up a wire 76. Via suitably placed rolls 77 or similar elements said wire 76 is connected to the second, proximal brace element 37 or the second coupling element 39, which as a result is pulled to the left, thereby compressing the spring force assembly. The dimensions of the cavity, the block, and the spring force assembly, the position of the cograil 74 and the cogwheel 75, the diameter of the bobbin, and the gear ratio between cogwheel 75 and bobbin, etc. are chosen such that during the linear displacement of both the second brace element 37 and the stopper 12 of the cartridge along the longitudinal axis to the left, the brace element 37 does not touch the stopper, or if touching it, does only exert a strongly reduced bias force.

For activating the spring force assembly, the cogwheel 75 is temporarily decoupled from the bobbin 78, thereby releasing the second brace element 37. For example the block 72 may be provided with a cam that interacts with a mechanism on the structure when reaching a certain position in the cavity, the mechanism decoupling cogwheel and bobbin when activated, and coupling them when deactivated. Alternatively such a cam or similar element may cause the coupling of cogwheel and bobbin as long as a certain position is not yet reached.

Figure 14:
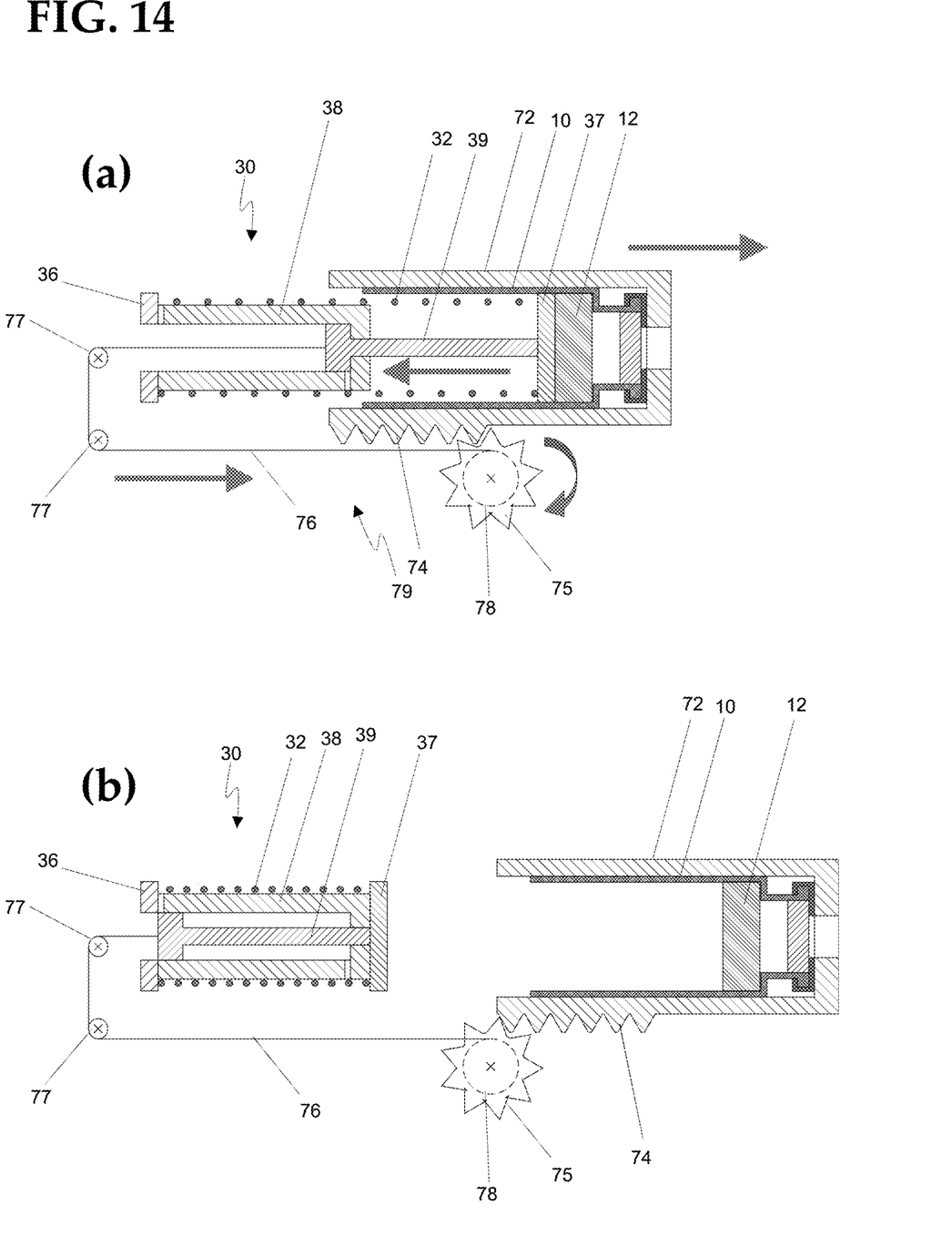
FIG. 14 schematically shows a longitudinal section of another advantageous mechanism in an infusion pump device according to the disclosure, for compressing a spring force assembly while removing a cartridge, without biasing the displaceable stopper of the cartridge, (a) before the spring force assembly has been tensioned, and (b) after the spring force assembly has been tensioned.

An alternative variant of such an approach is shown in FIG. 14, where the wire 76 is winded up onto the bobbin 78 in the reversed direction, compared to the embodiment in FIG. 13. In this approach the removal of the cartridge holding block 72 with the emptied cartridge from the cavity 19 rotates the cogwheel 75, winds up the wire 76, and retracts the brace element 37 facing the stopper 12, thereby recompressing the spring force assembly. A suitable mechanism, for example a ratchet mechanism or the like, locks the cogwheel 75 when the block and the thus the cograil 74 is removed, and prevents the wire 76 from unwinding and the spring force assembly from expanding.

The embodiments of infusion pump devices according to the disclosure as shown in FIGS. 12 to 14 have been realized with spring force assemblies according to the disclosure. However, the same functional principle can also be applied to prior art spring elements, such as mere helical compression springs. Particularly when the spring element is compressed by a wire coupled to the cartridge holding block, the wire itself, arranged in the spring, restricts the kinking and buckling of the compressed spring element. In a particularly suitable variant of such an approach, a shaft is provided inside the spring element, and/or a sleeve outside the spring element, which additionally stabilizes the spring element.

In specific embodiments, compressing the spring element may be achieved, in dependence of the overall design of the spring force assembly, by exerting a pushing force and/or a pulling force.

In an advantageous variant of such an assembly the first coupling element and the second coupling element are operationally coupled to each other in such a way that they restrict the distance between the first brace element and the second brace element to a certain minimum value, thereby restricting the possible compression of the spring element.

The coupling elements can be attached to their corresponding brace elements by any suitable fastening means, for example with a screw joint, weld joint, adhesive bond, or press fit. Corresponding brace elements and coupling elements can also be realized as a single integral component.

A spring force assembly according to the disclosure can comprise one or more intermediate coupling elements that operationally couple the first coupling element and the second coupling element.

The coupling elements can be are arranged on the inner side of the spring element or on the outer side of the spring element.

Advantageously in a spring force assembly according to the disclosure the coupling elements are operationally coupled in such a way that they form a telescopic arrangement.

A spring force assembly according to the disclosure can comprise two or more spring elements. A spring force assembly according to the disclosure can comprise at least two spring elements or at least two or more spring elements. Advantageously the coupling elements are arranged between two spring elements.

The spring element of a spring force assembly according to the disclosure can comprise one or more helical compression springs.

In a particular variant of a spring force assembly according to the disclosure, a spring element comprises two helical compression springs that are aligned to each other, wherein one of said two springs is arranged inside the other one of said two springs.

Embodiments provided herein describe an infusion pump comprising a spring force unit for biasing a displaceable stopper of a liquid medicine cartridge, wherein the spring force unit is a spring force assembly comprising a spring element arranged along a longitudinal axis, comprising: a first brace element arranged on one longitudinal end of the spring element; a second brace element arranged on the other longitudinal end of the spring element; a first coupling element attached to the first brace element and aligned to the longitudinal axis; and a second coupling element attached to the second brace element and aligned to the longitudinal axis; and wherein the first coupling element and the second coupling element are operationally coupled to each other in such a way that they restrict the distance between the first brace element and the second brace element to a certain maximum value, thereby also restricting the possible expansion of the spring element.

An advantageous embodiment of a spring force assembly according to the disclosure comprises a locking mechanism for releasably locking the spring force assembly in a compressed state and/or a partially expanded state.

In another advantageous embodiment of a spring force assembly according to the disclosure, an outer sleeve is attached to one of the brace elements, the outer sleeve covering the spring element in the compressed state.

The different parts of a spring force assembly according to the disclosure can be made of metal, such as brass, steel or aluminum. The parts, typically except the spring element, can also be made of suitable plastics. Advantageously polymer parts are manufactured by injection molding. In some embodiments, the spring element is made of special-purpose high-performance plastics.

An infusion pump device according to the disclosure comprises a spring force unit for biasing a displaceable stopper of a liquid medicine cartridge. Advantageously the spring force unit is a spring force assembly according to the disclosure, as discussed above.

In an advantageous embodiment of the device a locking mechanism is provided for releasably locking the spring force unit in a compressed state and/or a partially expanded state.

In embodiments described here, methods or devices provided herein can comprise the spring force assembly housed within an infusion pump.

In another advantageous embodiment of an infusion pump device according to the disclosure a compressing mechanism is provided, for compressing the spring force unit. The mechanism comprises a cartridge holding block in which a liquid medicine cartridge can be mounted; an open cavity in which the spring force unit is mounted with one distal end of the spring force unit abutting the bottom of the cavity, and into which the cartridge holding block can be inserted in a linear motion; and with a mechanism for converting a linear displacement of the cartridge holding block along a longitudinal axis of the cavity into a linear displacement of the second, proximal end of the spring force unit toward the bottom of the cavity.

In a particularly advantageous variant of such a infusions pump device, the converting mechanism comprises a cograil arranged on the cartridge holding block along a longitudinal axis of the block; a cogwheel that operationally interacts with the cograil, being rotated when the block is linearly displaced along the cavity axis in one direction; a bobbin releasably rotationally coupled to the cogwheel; and a wire connected to said bobbin and to the second, proximal end of the spring force assembly 30, in such a way that when the bobbin is rotated due to the rotation of the cogwheel and winds up the wire, the wire pulls the second, proximal end of the spring force unit toward the cavity bottom, thereby compressing the spring force unit.

In a use according to the disclosure of a spring force assembly, the spring force assembly is used for biasing a displaceable stopper of a liquid container or a syringe.

In another use according to the disclosure of a spring force assembly, the spring force assembly is used in an infusion pump device, for example an infusion pump device according to the disclosure.

The present disclosure is not to be limited in scope by the specific embodiments described herein. Indeed, various modifications of the present disclosure, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

LIST OF REFERENCE NUMERALS 2 infusion pump device
4 dosing unit
6 upstream fluidic system
8 downstream fluidic system
10 disposable rigid cartridge, liquid medicine container, primary reservoir
10a distal end
10b proximal end
11 reservoir volume
12 displaceable stopper
13 fluidic connector
14 pierceable membrane or septum
16 helical compression spring
18 casing structure
19 cavity
19a bottom of cavity
19b opening of cavity
20 connector
22 infusion tubing
24 infusion site
26 patient, user
30 spring force assembly
32 spring element
33 helical spring
35 longitudinal axis
36 first brace element
37 second brace element
37a truncated cone
38 first coupling element
39 second coupling element
40a shaft
40a' tube element
40b disk
40b' protruding shoulder
41a tube element
41a' beam
41b protruding shoulder
41b' protrusion
41c ramp
42, 42' venting bore
43, 43' central bore
45 intermediate coupling element
46a tube element
46b protruding shoulder
46c protruding shoulder
47 O-ring seal
48 sleeve
50 locking element
60 high precision dosing unit
61 piston pump
62 pump cylinder
65 ¾-way valve
64 piston
66 piston rod
68 actuation unit
70 threaded cap
71 thread
72 cartridge holding block
73 holding element
74 cograil
75 cogwheel 76 wire
77 roll
78 bobbin
79 compressing mechanism
80 slidable gate element
81 spring
82 cam
84 opening
$d_{min}$ minimum elongation
$d_{max}$ maximum elongation

The invention claimed is:

1. An infusion pump device, comprising a spring force unit for biasing a displaceable stopper of a liquid medicine cartridge, wherein the spring force unit is a spring force assembly comprising a spring element arranged along a longitudinal axis, comprising:
   a first brace element is arranged on and supports one longitudinal end of the spring element;
   a second brace element is arranged on the other longitudinal end of the spring element;
   a first coupling element attached to the first brace element and aligned to the longitudinal axis; and
   a second coupling element attached permanently to the second brace element and aligned to the longitudinal axis; and
wherein the first coupling element and the second coupling element are each single-piece elements operationally coupled to each other in such a way that they restrict the distance between the first brace element and the second brace element to a certain maximum value, thereby also restricting the possible expansion of the spring element.

2. The infusion pump device according to any of claim 1, further comprising:
   a compressing mechanism for compressing the spring force unit, with a cartridge holding block in which the liquid medicine cartridge can be mounted;
   an open cavity in which the spring force unit is mounted with one distal end of the spring force unit abutting the bottom of the cavity, and into which the cartridge holding block can be inserted in a linear motion; and
   a mechanism for converting a linear displacement of the cartridge holding block along a longitudinal axis of the cavity into a linear displacement of the proximal end of the spring force unit toward the bottom of the cavity.

3. The infusion pump device of claim 1, wherein the first coupling element and the second coupling element are operationally coupled to each other in such a way that they restrict the distance between the first brace element and the second brace element to a certain minimum value, thereby restricting the possible compression of the spring element.

4. The infusion pump device of claim 1, wherein the coupling elements are operationally coupled in such a way that they form a telescopic arrangement.

5. The infusion pump device of claim 1, wherein the spring element comprises one or more helical compression springs.

6. The infusion pump device of claim 1, wherein the spring force unit has a damper configured to allow only a certain maximum displacement velocity during expansion of the spring element along the longitudinal axis.

7. The infusion pump device of claim 1, wherein the first coupling element has at least one venting bore.

8. The infusion pump device of claim 1, wherein the first coupling element has at least one venting bore for pressure relief, and wherein the first coupling element, second coupling element and the at least one venting bore interact together as a damper configured to allow only a certain maximum displacement velocity during expansion of the spring element along the longitudinal axis.

9. The infusion pump device of claim 1, wherein:
   the coupling elements are operationally coupled in such a way that they form a telescopic arrangement,
   the first coupling element is provided with at least one venting bore for pressure relief, and
   the first coupling element, second coupling element and the at least one venting bore interact together as a damper configured to allow only a certain maximum displacement velocity during expansion of the spring element along the longitudinal axis.

* * * * *